United States Patent [19]

Chucholowski

[11] Patent Number: 4,950,675
[45] Date of Patent: Aug. 21, 1990

[54] PYRIDINE DI-MEVALONO-LACTONES AS INHIBITORS OF CHOLESTEROL BIOSYNTHESIS

[75] Inventor: Alexander Chucholowski, Ypsilanti, Mich.

[73] Assignee: Warner-Lambert Company, Morris Plains, N.J.

[21] Appl. No.: 287,497

[22] Filed: Dec. 21, 1988

[51] Int. Cl.$^5$ .................. C07D 405/14; A61K 31/445
[52] U.S. Cl. ..................................... 514/336; 546/268; 546/307; 546/312; 546/341; 546/342; 546/193; 546/194; 546/256; 546/284; 546/281; 514/352; 514/353; 514/277; 514/343; 514/318; 514/333; 514/256; 514/232.2; 544/124; 544/333; 544/357; 544/360; 540/597
[58] Field of Search ................ 546/268, 281; 540/597; 514/336, 236, 256, 236; 544/124, 357, 360

[56] References Cited

PUBLICATIONS

Merk Index. 9th Edition, p: 7853.
F. H. Hulcher, *Arch. Biochem. Biophys.* 30 (1971), 146, 422.
Brown et al., *J. Chem. Soc. Perkin I,* (1976), 1165.
M. S. Brown & J. L. Goldstein, *New England Journal of Medicine* (1981), 305, No. 9, 515–517.
*Journal of the American Medical Association* (1984), 251, No. 3, 351–374.
F. M. Singer et al., *Proc. Soc. Exper. Biol. Med.* (1959), 102, 370.

*Primary Examiner*—Jane T. Fan
*Attorney, Agent, or Firm*—Ruth H. Newtson

[57] ABSTRACT

Certain trans-6,6'-[[(substituted)pyridin-3,5-diyl]-dialkane- and dialkene-diyl]bis [tetrahydro-4-hydroxypyran]-2-ones and the corresponding ring-opened acids derived therefrom are potent inhibitors of the enzyme 3-hydroxy-3-methyl-glutaryl-coenzyme A reductase (HMG-CoA reductase) and are useful as hypocholesterolemic and hypolipidemic agents.

7 Claims, No Drawings

PYRIDINE DI-MEVALONO-LACTONES AS INHIBITORS OF CHOLESTEROL BIOSYNTHESIS

BACKGROUND OF THE INVENTION

The present invention relates to compounds and pharmaceutical compositions useful as hypocholesterolemic and hypolipidemic agents. More particularly, this invention concerns certain trans-6,6'-[[(substituted)-pyridin-3,5-diyl]dialkane- and dialkene-diyl]bis[tetrahydro-4-hydroxy-pyran-2-ones] and the corresponding ring-opened acids derived therefrom which are potent inhibitors of the enzyme 3-hydroxy-3-methylglutaryl-coenzyme A reductase (HMG-CoA reductase), pharmaceutical compositions containing such compounds, and a method of lowering blood serum cholesterol levels employing such pharmaceutical compositions.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine* (1981), 305, No. 9, 515–517). It has now been established that lowering LDL-C levels affords protection from coronary heart disease (cf. *Journal of the America Medical Association* (1984) 251, No. 3, 351–374).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer, et al, *Proc. Soc. Exper. Biol. Med.* (1959), 102, 370–373) and F. H. Hulcher, *Arch. Biochem. Biophys.* 30 (1971) 146, 422).

U.S. Pat. Nos. 3,983,140; 4,049,495; and 4,137,322 disclose the fermentative production of a natural product, now called compactin, having an inhibitory effect on cholesterol biosynthesis. Compactin has been shown to have a complex structure which includes a mevalonolactone moiety (Brown, et al, *J. Chem. Soc. Perkin I*, (1976), 1165).

U.S. Pat. No. 4,255,444 to Oka, et al, discloses several synthetic derivatives of mevalonolactone having antilipidemic activity.

U.S. Pat. Nos. 4,198,425 and 4,262,013 to Mitsue, et al, disclose aralkyl derivatives of mevalonolactone which are useful in the treatment of hyperlipidemia.

U.S. Pat. No. 4,375,475 to Willard et al. discloses certain substituted 4-hydroxytetrahydropyran-2-ones which, in the 4(R)-trans stereoisomeric form, are inhibitors of cholesterol biosynthesis.

U.S. Pat. No. 4,647,576 to Hoefle, et al, discloses certain trans-6-[2-(substituted)-pyrrol-1-yl]alkyl]tetrahydro-4-hydroxypyran-2-ones and the corresponding lactone ring-opened acids as inhibitors of cholesterol biosynthesis.

U.S. Pat. No. 4,681,893 to Roth discloses certain trans-6-[[2-, (3-, or (4-carboxamido-substituted)pyrrol-1-yl]alkyl- or alkenyl]-tetrahydro-4-hydroxypran-2-one inhibitors of cholesterol biosynthesis.

SUMMARY OF THE INVENTION

In accordance with the present invention, there are provided certain trans-6,6'-[[2(substituted)pyridin-3,5-diyl]dialkane- and dialkene-diyl]bis[tetrahydro-4-hydroxypyran-2-ones] and the corresponding ring-opened hydroxy-acids derived therefrom which are potent inhibitors of cholesterol biosynthesis by virtue of their ability to inhibit the enzyme 3-hydroxy-3-methylglutaryl coenzyme A reductase (HMG-CoA reductase).

In particular, in its broadest chemical compound aspect, the present invention provides compounds of structural Formula I

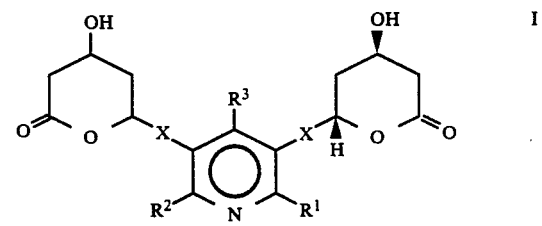

wherein X is —CH$_2$CH$_2$— or —CH=CH— (preferably in the (E) trans configuration).

R$_1$, R$_2$ and R$_3$ independently are alkyl of from one to six carbons; trifluoromethyl; cyclopropyl; cyclohexyl; cyclohexylmethyl; NR'R" where R' and R" are each independently hydrogen, alkyl of from one to four carbon atoms, or together with the N to which they are

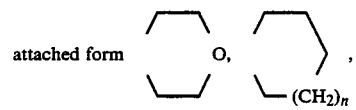

wherein n' is an integer of from 0 to 5,

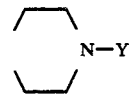

wherein Y is hydrogen or an alkyl of from one to four carbon atoms; phenyl; or, each of R$_1$, R$_2$ and R$_3$ is phenyl substituted with fluorine, chlorine, bromine, hydroxy, trifluoromethyl, alkyl of from one to four carbon atoms, or alkoxy of from one to four carbon atoms; phenylmethyl; phenylmethyl substituted with fluorine, chlorine, bromine, hydroxy, trifluoromethyl, alkyl of from one to four carbon atoms, or alkoxy of from one to four carbon atoms; 2-, 3-, or 4-pyridinyl; 2-, 4-, or 5-pyrimidinyl; or 2-, or 3-thienyl; and the corresponding N-oxides; with the proviso that R$_3$ cannot represent NR'R".

Also contemplated as falling within this aspect of the invention are the corresponding bis (dihydroxy-acid) compounds of Formula II corresponding to the opened form of the lactone ring of compounds of Formula I

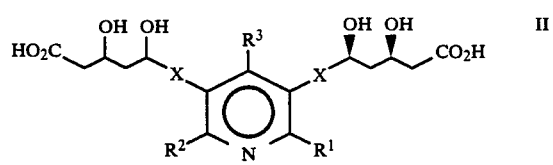

where X, R$_1$, R$_2$, and R$_3$ are as defined above, the lower alkyl esters and pharmaceutically acceptable salts thereof, and the corresponding N-oxides.

In another aspect of the present invention, there is provided a method of preparing compounds of Formula I above by (a) first reacting a substituted [(pyridin- 3,5-yl) dialkane- or dialkene-diyl aldehyde compound of Formula VII

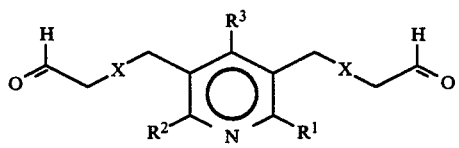

where X, $R_1$, $R_2$, and $R_3$ are as defined above, with the alkali metal salt of the dianion of methyl acetoacetate to form a compound of structural Formula VIII

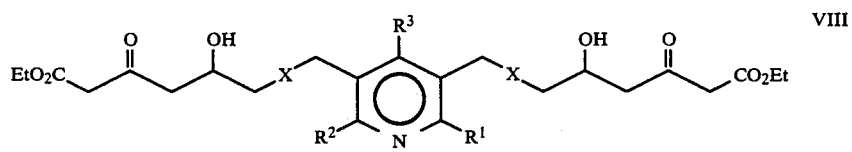

where X, $R_1$, $R_2$ and $R_3$ are as defined above, then successively (b) reducing compound VIII with a trialkylborane and sodium borohydride and (c) oxidizing with alkaline hydrogen peroxide to produce an ester compound of Formula IX

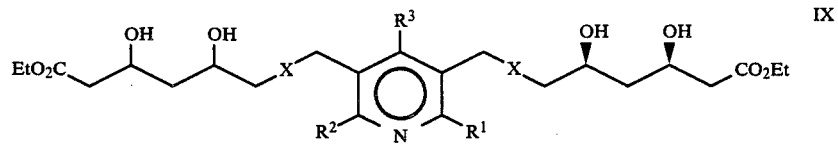

and finally (d) hydrolyzing and cyclizing, if desired, the ester compound of Formula IX to a bis lactone compound of Formula I by heating in an inert solvent, and if desired, converting the bis lactone compound to the corresponding ring-opened bis (dihydroxy-acid) compounds of Formula II or, alternatively converting, if desired, the acid to a pharmaceutically acceptable salt.

In another aspect, the present invention provides pharmaceutical compositions, useful as hypolipidemic or hypocholesterolemic agents, comprising a hypolipidemic or hypocholesterolemic effective amount of a compound in accordance with this invention as set forth above, in combination with a pharmaceutically acceptable carrier.

In another aspect, the present invention provides a method of inhibiting cholesterol biosynthesis in a patient in need of such treatment by administering a pharmaceutical composition in accordance with the present invention as defined above.

DETAILED DESCRIPTION

In a first preferred subgeneric chemical compound aspect, the present invention provides compounds of Formula I above wherein X is —CH$_2$CH$_2$—, and $R_1$, $R_2$ and $R_3$ are as defined above and the configuration in the lactone ring is R*R*.

In a second preferred subgeneric chemical compound aspect, the present invention provides compounds of Formula I above where X is. —CH=CH—, most preferably in the (E)-trans form and the configuration in the lactone ring is R*S*.

As used throughout this specification and the appended claims, the term "alkyl" denotes a branched or unbranched saturated hydrocarbon group derived by the removal of one hydrogen atom from an alkane. The term "lower alkyl" denotes alkyl of from one to four carbon atoms.

The term "alkoxy" denotes an alkyl group, as just defined, attached to the parent molecular residue through an oxygen atom.

The compound of Formula I of the present invention wherein each lactone moiety contains at least one chiral center includes stereoisomers due to the presence of the asymmetric carbon atom and can exist as each optical isomer or a racemic mixture. Further, a compound of Formula I having not less than two asymmetric carbon atoms in its molecule may exist as each diastereomer(s) or the mixture thereof. The mixture of the diastereomers can be resolved to each racemic compound by conventional resolution methods such as chromatography or fractional recrystallization and the like and the racemic compound can be resolved into each optical isomer by a conventional method for racemic resolution by fractional recrystallization of a salt of the racemic compound with an optically active acid, e.g, tartaric acid or camphor sulfonic acid. The compound of Formula I, as used to describe the present invention, is understood to include such isomers or diastereomers.

Compounds of the present invention in which X is —CH=CH— are prepared by the general synthetic method outlined in Reaction Scheme 1. The preparation of compounds of the present invention where X is —CH$_2$CH$_2$— is outlined in Reaction Scheme 2.

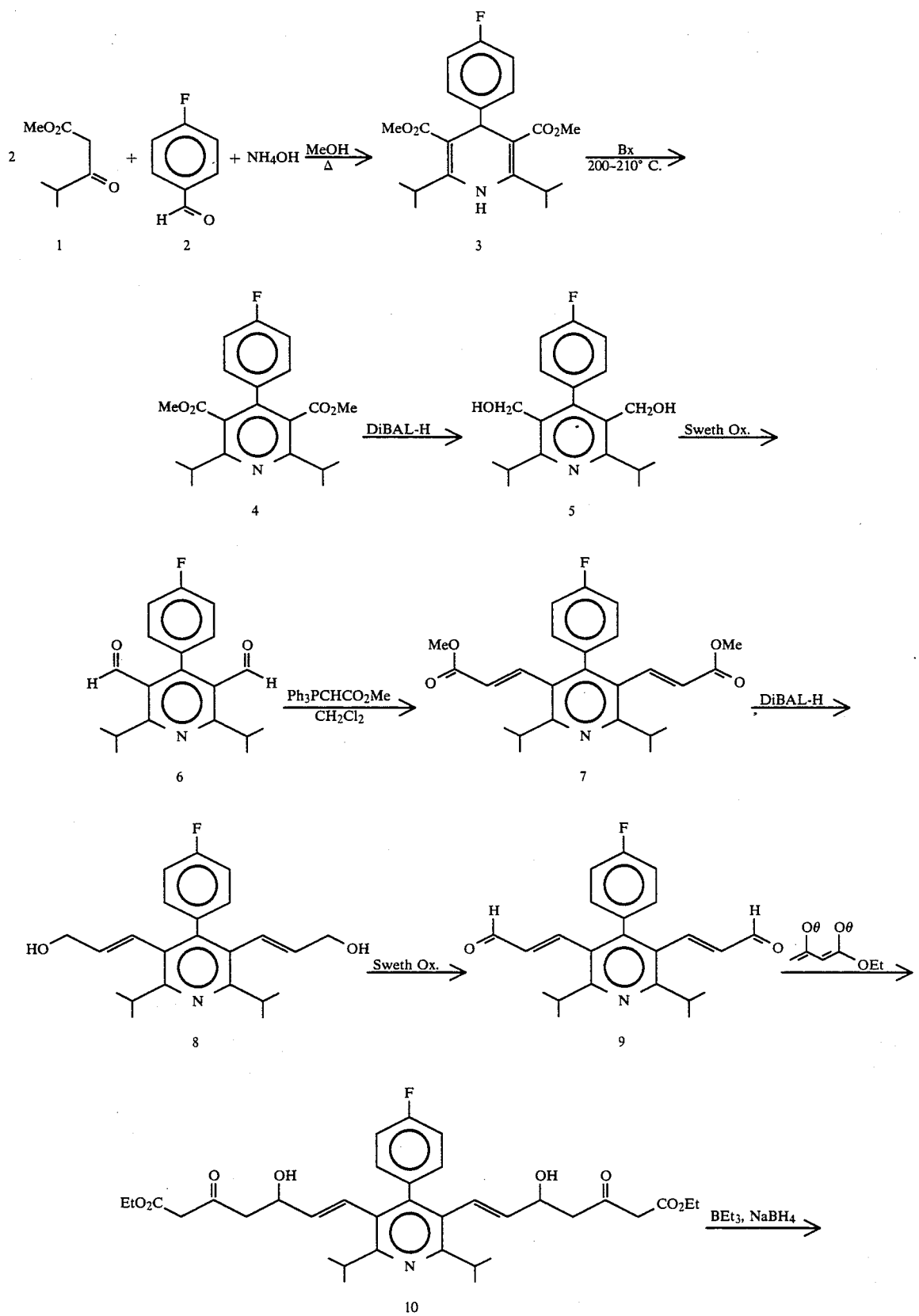

-continued
Reaction Scheme 1

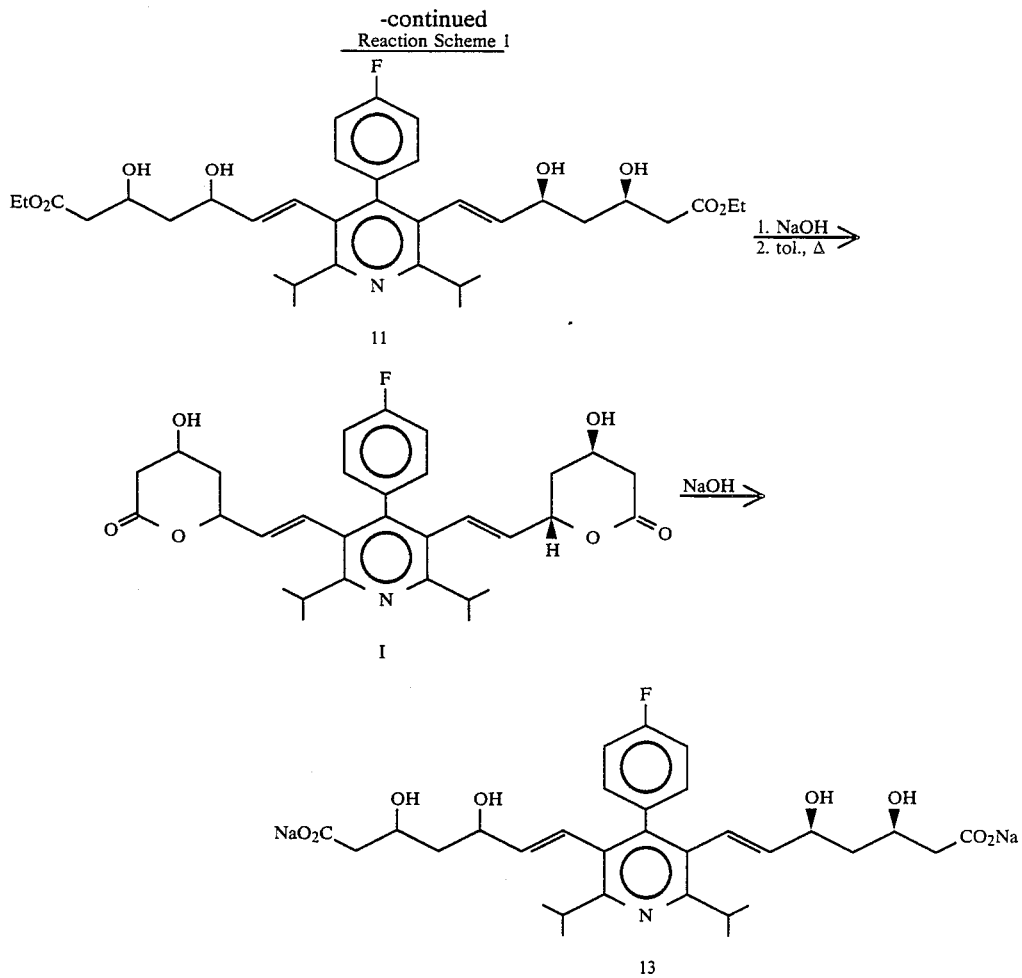

Referring to Reaction Scheme 1, the 3-oxoalkanoic acid ester, represented by 4-methyl-3-oxopentanoic acid methyl ester, 1, and ammonium hydroxide are reacted with a suitable aldehyde, represented by 4-fluorobenzaldehyde, 2, by heating the mixture in a suitable solvent such as methanol.

The resulting dihydropyridine, 3, is then aromatized by heating with a suitable dehydrating agent such as powdered sulfur at a temperature between 130° C. and 210° C.

The resulting pyridine, 4, is converted to the corresponding 3,5-di-alcohol, 5, employing a suitable reducing agent such as lithium aluminum hydride or diisobutyl aluminum hydride in a polar solvent such as dichloromethane under nitrogen at low temperature.

The di-alcohol, 5, is then oxidized to the corresponding dialdehyde by generally known methods. Using the method of Swern (Swern, et al, *J. Org. Chem.*, 43: 2480, 1978) where activated dimethylsulfoxide is the oxidant, Yields the desired dialdehyde, 6.

Wittig reaction of the dialdehyde, 6, with a stabilized ylide such as carbomethoxy triphenylphosphorane in dichloromethane at room temperature produces the unsaturated trans-di-ester, 7, in high field. The ester, 7, is reduced to the di-allyl alcohol, 8, using a well-known procedure employing two equivalents of diisobutyl aluminum hydride at −78° C.

The di-allyl alcohol, 8, is reoxidized to the dialdehyde, 9, by swern oxidation, followed by an aldol condensation to the sodium lithium dianion of ethyl acetoacetate at −78° C. in tetrahydrofuran (see Kraus, et al, *J. Oro. Chem.*, 48:2111 (1983)) to form the 3,5-diester, di-(5-hydroxy-3-oxo-6-heptenoio acid-ethyl ester), 10.

The product of this condensation is then reduced in a sequence of steps in which it is first dissolved in a polar solvent such as tetrahydrofuran with a catalytic amount of 2,2-dimethylpropanoic acid under a dry atmosphere. A small excess of triethylborane is then added. The mixture is stirred at room temperature for a short period, after which it is cooled to a temperature preferably between about −60° C. and −8° C. Dry methanol is added, followed by sodium borohydride, the resulting mixture is kept at low temperature for 4–8 hours before treating it with hydrogen peroxide and ice water. The substituted 3,5-dihydroxy-6- heptenoic acid ethyl ester, 11, is isolated having the preferred R*,S* configuration.

The ester, 11, may be utilized as such in the pharmaceutical method of this invention, or may be converted, if desired, to the corresponding acid, 12, employing stepwise basic hydrolysis and acidification by generally well-known methods, and the free acid can be dehydrated to the 6,6'-bis-tetrahydro-4-hydroxypyran-2-one, I, by heating in an inert solvent such as toluene with concomitant azeotropic removal of water. The bis-pyranone may be converted to the ring-opened bis(-dihydroxy-acid) salt form 13 be treatment with a base such as sodium hydroxide in a suitable solvent such as methanol.

Referring to Reaction Scheme 2, the unsaturated pyridine esters, 7, obtained by methods described above in Reaction Scheme 1, are reduced by the action of hydrogen over Pd/C to produce the corresponding salurated pyridine ester compounds, 14. The saturated esters, 15, are reduced by the action of diisobutyl aluminum hydride to the corresponding alcohols, 15, which in turn are converted through the same reaction sequence shown in Reaction Scheme 1 to the compounds of this invention.

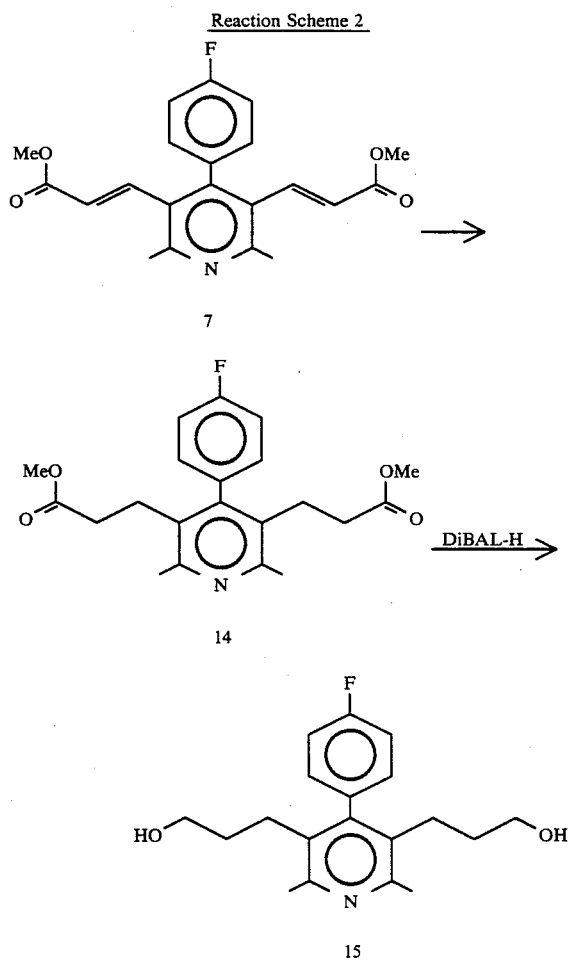

In the ring-opened dihydroxy acid form, compounds of the present invention react to form salts with pharmaceutically acceptable metal and amine cations formed from organic and inorganic bases.

The N-oxide substituent may be obtained by treating the nitrogen containing compound with peracids, such as metachloroperbenzoic acid, pertrifluoroacetic acid and the like. Conditions are as in analogous reactions.

Notably the above schemes and corresponding discussions illustrate the preparation of the most preferred compound of the invention. But one of ordinary skill in the art would readily use analogous reactants and conditions to make up the remaining compounds of Formula I and Formula II defined above. Numerous references are available showing such reactions.

The term "pharmaceutically acceptable metal cation" contemplates positively charged metal ions derived from sodium, potassium, calcium, magnesium, aluminum, iron, zinc and the like.

The term "pharmaceutically acceptable amine cation" contemplates the positively charged ions derived from ammonia and organic nitrogenous bases strong enough to form such cations. Bases useful for the formation of pharmaceutically acceptable nontoxic bas addition salts of compound s of the present invention form a class whose limits are readily understood by those skilled in the art. (See, for example, Berge, et al, "Pharmaceutical salts," *J. Pharm. Sci.*, 66: 1–19 (1977)).

The free acid form of the compound may be regenerated from the salt, if desired, by containing the salt with a dilute aqueous solution of an acid such as hydrochloric acid.

The base addition salts may differ from the free acid form of compounds of this invention in such physical characteristics as melting point and solubility in polar solvent, but are considered equivalent to the free acid forms for purposes of this invention.

The compounds of this invention can exist in unsolvated as well as solvated forms. In general, the solvated forms, with pharmaceutically acceptable solvents such as water, ethanol, and the like, are equivalent to the unsolvated forms for purposes of this invention.

The compounds of this invention are useful as hypocholesterolemic or hypolipidemio agents by virtue of their ability to inhibit the biosynthesis of cholesterol through inhibition of the enzyme 3-hydroxy-3-methylglutaryl-coenzyme A reductase (HMG-CoA reductase).

The ability of compound s of the present invention to inhibit the biosynthesis of cholesterol was measured by a method (designated CSX screen) which utilizes the procedure described by R. E. Dugan, et al, *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of cholesterol-14C-acetate into nonsaponifiable lipid by the rat liver homogenate is measured. The micromolar concentration of compound required for 50% inhibition of sterol synthesis over a one-hour period is measured, and expressed as an IC50 value.

The ability of compound s of the present invention to inhibit the biosynthesis of cholesterol was also measured by a method (designated AICS screen) which utilizes the procedure described by A. W. Alberts et al, Proc. Natl. Acad. Sci., (1980), 77, pp 3957–3961.

In this method male Sprague-Dawley rats (200 g body weight) previously fed 5% cholestyramine for three days were randomly divided into groups (N=5/group) and given a single dose of vehicle (controls) or compound by an oral gavage at the indicated doses. One hour after drug dosing, all rats were injected intraperitoneally with sodium[1-$^{14}$C]-acetate (18.75 $\mu$Ci/rat in 0.2 ml saline). After 50 minutes, blood samples were taken, plasma obtained by centrifugation, and plasma [$^{14}$C] cholesterol measured after saponification and extraction.

The activities of several representative examples of compound s in accordance with the present invention appear in Tables 1 and 2.

TABLE 1

| X | R₁ | R₂ | R₃ | AICS [1.0 mg/kg] % Inhibition of Cholesterol Synthesis |
|---|---|---|---|---|
| —CH=CH— | —CH(CH₃)₂ | —CH(CH₃)₂ | 4-Fluorophenyl | −65% |
| —CH=CH— | —CH₂CH₃ | —CH₂CH₃ | 4-Fluorophenyl | −3% |

TABLE 2

| X | R₁ | R₂ | R₃ | CSI IC₅₀ µMole/L | AICS (1.0 mg/kg) % Inhibition of Cholesterol Synthesis |
|---|---|---|---|---|---|
| —CH=CH— | —CH(CH₃)₂ | —CH(CH₃)₂ | 4-Fluorophenyl | 0.0056 | −21% |
| —CH=CH— | —CH₂CH₃ | —CH₂CH₃ | 4-Fluorophenyl | 0.032 | −16% |

For preparing pharmaceutical compositions from the compound s described by this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents, it can also be an encapsulating material.

In powders, the carrier is a finely divided solid which is in a mixture with finely divided active compound. In tablets, the active compound is mixed with the carrier having the necessary binding properties in suitable proportions and compacted in the shape and size desired.

For preparing suppository preparations, a low-melting wax such as a mixture of fatty-acid glycerides and cocoa butter is first melted, and the active ingredient is dispersed homogeneously therein, as by stirring. The molten homogeneous mixture is then poured into convenient sized molds and allowed to cool and solidify.

The powders and tablets preferably contain 5 to about 70% of the active ingredient suitable solid carriers are magnesium carbonate, magnesium stearate, talc, sugar, lactose, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as carrier providing a capsule in which the active component (with or without other carriers) is surrounded by a carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

In therapeutic use as hypolipidemic or hypocholesterolemic agents, the compound s utilized in the pharmaceutical method of this invention are administered to the patient at dosage levels of from 40 mg to 60 mg per day. For a normal human adult of approximately 70 kg of body weight, this translates to a dosage of from about 0.5 mg/kg to about 8.0 g/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of
6,6'-[[2,6-bis(1-methylethyl)-4-(4-fluorophenyl)-3,5-pyridinediyl]di-1,2-ethenediyl]bis [4α,6B(E)] tetrahydro-4-hydroxy-2H-pyran-2-one]

Step 1—Preparation of 3,5-Dicarbomethoxy-1,4-Dihydro-4-(4-fluorophenyl)-2,6-bis(1-methylethyl),pyridine A mixture of 152 g (1.05 mole) 4-methyl-3-oxopentanic acid methyl ester, 56 ml (1.05 mole) 4-fluoro benzaldehyde and 40 ml conc. ammonium hydroxide was heated to reflux in 200 ml methanol for 48 hours. The reaction mixture was then concentrated in vacuo, the viscous residue was dissolved in 500 ml ethylether and washed with saturated sodium bisulfite. The organic layer was dried over magnesium sulfate, filtered and evaporated to yield 202 g of the Step 1 title product. Analysis for $C_{21}H_{26}FNO_4$. calc; C, 67.18; H, 6.98; N, 3,73. Found: C, 67.40; H, 7.48; N, 3.88.

Step 2—Preparation of 3,5-Dicarbomethoxy-4-(4-fluorophenyl)-2,6-bis(1-methylethyl)pyridine A mixture of 300 g dihydropyridine of Step 1 and 2 g freshly sublimed sulfur in 100 ml xylene was heated to 200°–210° C. for 30 minutes. When the development of hydrogen sulfide had subsided, the reaction mixture was cooled to room temperature, and ca. 100 g of Charcoal plus 1000 ml of ethyl acetate was added. This mixture was heated to reflux for 6 hours and then filtered through Celite filter aid. The filtrate was concentrated under vacuum and the residue was chromatographed on silica-gel, eluting with ethyl acetate/hexane to yield 78 g of the Step 2 title product.

NMR(CDCl$_3$) 7.1δ (multiplet, 4 protons), 3.45 (singlet, 6 protons), 3.03 (quintst, J=7 Hz, 2 protons); 1.30 (doublet, J=−7 Hz, 12 protons).

Step 3—Preparation of 4-(4-Fluorophenyl)-3,5-di(hydroxymethyl)-2,6-bis(1-methylethyl)pyridine 55.2 g(0.148 mol) of the Step 2 title product was dissolved in 500 ml of dry diohloromethane and cooled to −78° C. A solution of 620 ml 1M di-isobutyl aluminum hydride in dichloromethane under nitrogen was added dropwise. After addition, tho reaction mixture was stirred at −78° C. for 15 minutes, the cooling bath was removed, and the mixture was allowed to warm to 0° C. and then quenched with a concentrated aqueous solution of sodium sulfate (150 ml). The mixture was diluted with tetrahydrofuran and filtered. The filtrate was concentrated in vacuo Yielding the Step 3 title product as a white solid. Yield: 26.5 g (56%); m.p. 55°–156° C.

Step 4—Preparation of 4-(4-Fluorophenyl)-2,6-bis(1-methylethyl) pyridine-3,5-dicarboxaldehyde To solution of 16 ml (0.18 mol) oxalyl chloride in 150 ml dry diohloromethans was added, et −78° C., 40 ml dimethyl sulfoxide over a period of 5 minutes. After 10 minutes, 26 g (0,082 mol) of the product of step 3 in 200 ml of 1:3 solution dimethyl sulfoxide/dichloromethane was added dropwise. This reaction mixture was stirred at −78° C. for 20 minutes, before it was quenched with 80 ml triethylamime. The cooling bath was removed and the reaction was allowed to warm to room temperature. The reaction was partitioned between ethyl acetate (500 ml) and 1N hydrochloric acid (200 ml). The organic layer was washed With water (4×100 ml) and brine and dried over magnesium sulfate and filtered. Evaporation of the filtrate in vaouo gave 24.5 g of the Step 4 title product as a viscous oil which was used without further purification.

NMR(CDCl$_3$): 9.73 δ (singlet, 2 protons); 7.1 (multiplet, 4 protons); 3.83 (quintet, 2 protons, 2H); 1.27 (doublet, 12 protons).

Step 5—Preparation of (E)-3,3-[2,6-bis(1-Methylethyl)-4-(4-fluorophenyl)-3,5-pyridinediyl]bis[2-propenoate, methylester]

24.5 g (0.078 mol) of the product of step 4 was dissolved in a solution of 52 g carbomethoxy triphenylphosp,horane in 800 ml dichloromethane. The reaction mixture was heated to reflux for 24 hours and then stirred at room temperature for another 48 hours. The solution was then taken up in ethyl acetate (300 ml) and washed with saturated aqueous NaHSO$_3$ (2×100 ml); then it was dried over magnesium sulfate, filtered and evaporated. The residual product was purified by flash chromotography on silica gel, eluting with ethyl acetate/hexane, to give 16.6 g of the Step 5 title ester product.

NMR (CDCl$_3$): 7.40 δ (doublet, J=165 Hz, 2 protons); 6.8–7.2 (multiplet, 4 protons); 5.57 (doublet, J=16.5 Hz, 2 protons); 3.67 (singlet, 1 proton); 3.25 (quintet, 2 protons); 1.27 (doublet, J=7 Hz, 12 protons).

Step 6—Preparation of (E)-3,3'-[2,6-bis(1-Methylethyl)-4-(4-fluorophenyl)-3,5-pyridinediylbis]bis [2-propen-1-ol]

A solution of 16.2 g (0.003 mol) of the propenoate ester product of Step 5 in 200 ml dichloromethane was cooled under a stream of nitrogen to −78° C. and 200 ml 1M di-isobutyl aluminum hydride in dichloromethane was added dropwise over 10 minutes. After 60 minutes the mixture was quenched with 50 ml saturated aqueous sodium sulfate solution. When the mixture had warmed to room temperature, it was filtered and the filtrate was concentrated to give 13.2 g of the title product of Step 6 as a white solid.

NMR (CDCl$_3$) 6.8–7.2 δ (multiplet, 4 protons); 6.23 (doublet, J=16.5 Hz, 2 protons); 5.42 (doublet of doublet, J=16.5 Hz, J=5 Hz, 2 protons); 4.0 (doublet, J=5 Hz, 4 protons); 3.28 (quintet, J=7 Hz, 2 protons); 1.27 (doublet, J=7 Hz, 12 protons).

Step 7—Preparation of (E)-3,3'-[2,6-bis(1-methyl-ethyl)-4-(4-fluorophenyl)-3,5-pyridinediyl]bis [2-propen-1-al]

To a stirred solution of 9.5 ml (0.1 mol) oxalyl chloride in 100 ml dichloromethane at −78° C. was added with vigorous stirring 30 ml dimethyl sulfoxide. After 10 minutes a solution of 13.2 g (0.036 mol) of the title propenol product of Step 6 in 200 ml dichloromethane was added, and the mixture stirred at −78° C. for 30 minutes, and then treated with 50 ml triethylamine. The cooling bath was removed and the mixture was stirred until it had warmed to 0° C., and then diluted With 150 ml saturated aqueous ammonium chloride solution. The organic layer was separated and washed three times with water, dried over magnesium sulfate, filtered and evaporated. The residue was purified by flash chromatography on silica gel, eluting with ethyl acetate/hexane to provide 8.90 g (0.024 mol) of the title product of Step 7 as white crystals, m.p. 122°–123° C.

Step 8—Preparation of (E)-7,7'-[2,6-bis(1-methylethyl)-4-(4-fluorophenyl)-3,5-pyridinediyl]bis[ethyl-5-hydroxy-3-oxo-6-heptenoate]

To a solution of 8.90 g (0.024 mol) of the title propenal product of Step 7 in 200 ml absolute tetrahydrofuran under nitrogen at −78° C. was added a tetrahydrofuran solution of 0.06 mol dianion of ethyl acetoacetate, prepared as described by G. Kraus et al (J. Org. Chem; (1983)2111). The resulting viscous emulsion, was stirred for 20 minutes and then quenched with 12 ml acetic acid. Extraction of the concentrated mixture with ethyl acetate and concentration of the combined extracts gave an oil, Which was further purified by chromatography to provide the Step 8 title product; yield: 6.85 g.

NMR (CDCl$_3$): 6.8–7.2 δ (multiplet, 4 protons); 6.27δ (doublet, J=16.5 Hz, 2 protons); 5.20 (doublet of doublets, J=16.5 Hz, J=6 Hz; 4.2–4.6 (multiplet, 2 protons); 4.13 (quintet, J=7.5 Hz, 4H); 3.3 (singlet, 4 protons); 3.2–3.4 (quintet, J=7 Hz, 2 protons); 2.41 (doublet, J=6 Hz, 4 protons); 1.25 (triplet, J=7.5 Hz, 6 protons); 1.25 (doublet, J=7 Hz, 12 protons.

Step 9—Preparation of [R*,S*(E)]-7,7'-[1,6-bis(1-methylethyl)-4-(4-fluorophenyl)-3,5-pyridinediyl]bis[3,5-dihydroxy-6-heptenoic acid, dimethyl ester]

(Regarding the stereochemistry, this double bonds are E, the substituents on the side chains are syn; the stereochemistry of 3,5-side chains to each other is not known).

To a solution of 6.40 g (0.0102 mol) of the step 8 title product and 2 g (0.002 mol) 2,2-dimethylpropanoic acid in 60 ml anhydrous tetrahydrofuran under dry air atmosphere was added 23 ml of triethylborane (1M in ietrahydrofuran) via a syringe in one portion. The resulting yellow solution was stirred at room temperature for 5 minutes and then cooled to −78° C. Absolute methanol (10 ml) was added, followed by 0.80 g (0.021 mol) sodium borohydride. The reaction mixture was stirred at −78° C. for 4 hours and then poured into a 1:1 mixture of 30% hydrogen peroxide and ice. This mixture was stirred for 2 hours and then partitioned between chloroform and saturated aqueous sodium bicarbonate solution. The organic layer was separated, washed with water until peroxide free, dried over anhydrous magnesium sulfate, and concentrated under vacuum to provide the Step 9 title product is a Yellow oil; yield: 65 g.

NMR (CDCl$_3$): 6.8–7.2δ (multiplet, 4 protons): 6.28δ (doublet, J=16.5 Hz, 2 protons); 5.17 (doublet of doublets, J=16.5 Hz, J=6 Hz, 2 protons); 3.8–4.5 (multiplet); 4.1 (quintet, J=7.5 Hz, 4 protons); 3.5–4 (multiplet); 3–3.5 (multiplet); 2.3 (doublet, J=6 Hz, 4 protons); 1.26 (triplet, J=7.5 Hz, 6 protons); 1.25 (doublet, J=7.0 Hz, 12 protons).

Step 10 Preparation of 6,6'-[[2,6-bis(1-methylethyl)-4-(4-fluorophenyl)-3,5-pyridinediyl]di-1,2-ethenediyl]bis[4α,β(E)][tetrahydro-4-hydroxy-2H-pyran-2-one]

(Regarding the stereochemistry, the double bonds are E, the substituents on the two rings are trans; the stereochemistry of the rings to each other is not known).

To 6.50 g (10.3 mmol) of the Step 9 title product in 50 ml of tetrahydrofuran was added 22 ml 1N sodium hydroxide solution and a small amount of ethanol to ensure homogeneity. After stirring for two hours, the reaction mixture was concentrated in vacuo. Water (20 ml) was added to the residue and the resulting mixture was extracted with 50 ml chloroform. The aqueous layer was treated with 22 ml 1N HCl and concentrated to dryness under reduced pressure. The residual product is 7,7'-[1,6-bis(1-methylethyl)-4-(4-fluorophenyl)-3,5-pyridinediyl]bis[3,5-dihydroxy-6-heptenoic acid]. Toluene was added to this solid residue, and the mixture heated under reflux with concomitant azeotropic removal of water for 2.5 hours. The organic solvent was removed under reduced pressure and the residue was purified by flash chromatography on silica gel, eluting in chloroform/iso-propanol and isolating the title product of Step 10 in pure form by solvent removal; yield: 3.15 g, m.p. 184°–186° C.

NMR (CDCl$_3$) 6.9–7.1δ (mulitplet, 4 protons); 6.37 (doublet, J=16.2 Hz, 2 protons); 5.34 (doublet of doublets, J=6 Hz, J=16.2 Hz 2 protons); 5.0–5.1 (multiplet, 2 protons); 4.1–4.2 (multiplet, 2 protons); 3.2–3.4 (multiplet, 2 protons); 2.61, 2.59 (4 protons); 1.4–1.8 (multiplet, 4 protons); 1.28 (doublet, J=6 Hz, 12 protons).

Analysis for $C_{31}H_{36}FNO_6$ calc: C, 69.26; H, 6.75, N, 2.61. Found: C, 69.07; H, 6.61; N, 2.62.

Infrared spectrum, principal absorption at 3400, 1719, 1511, 1252, 1067, 1040 and 972 reciprocal centimeters.

Step 11—Preparation of [R*,S*(E)]-7,7'-[2,6-bis(1-methylethyl)-2,4-(4-fluorophenyl)-3,5- pyridinediyl]bis [3,5-dihydroxy-6-heptenoio acid, disodium salt]

(Regarding the stereochemistry, the double bonds are E, the substituents on the side chains are syn; the stereochemistry of 3,5-side chains to each other is not known).

To a solution of 1.30 g (2.42 m mol) of the Step 10 pyranone product in 5 ml tetrahydrofuran was added 4.84 ml 1N sodium hydroxido and ca. 2 ml methanol. The mixture was stirred for 2 hours at room temperature and then concentrated in vacuo. The residue was taken up repeatedly in methanol and concentrated. Finally the residual concentrate was dried to provide the step 11 title product as an amorphous solid.

NMR (DMSO): 7.0–7.2δ (multiplet, 4 protons), 6.14 (doublet, J=16.2 Hz, 2 protons): 5.29 (doublet of doublets, J=16.2 Hz, J=6 Hz, 2 protons); 4.85 (singlet, 2 protons) 4.02 (quintet, J=6.0 Hz, 2 protons); 3.1–3.5 (multiplet); 1.96 (doublet of doublets, J=2 Hz, J=15 Hz, 2 protons); 1.75 (doublet of doublets, J=15 Hz, J=8 Hz, 2 protons): 0.9–1.4 (mulitplet, 4 protons); 1.2 (12 protons).

Infrared spectrum, principal absorption at 3200, 1715, 1620, 1462, 1347, 1190, 1026, and 787 reciprocal centimeters.

Mass spectrum: M/z (% base Peak): 1366 (2.8), 1236 (8.3), 726 (11.3), 640 (77), 618 (100), 596(35.4).

EXAMPLE 2

Preparation of 6,6'-[2,6-diethyl-4-(4-fluorophenyl)-3,5-pyridinediyl]-di[2,1-ethenediyl]bis[4α,6β(E)][tetrahydro-4-hydroxy-2H-pyran-2-one]

(Regarding the stereochemistry, the double bonds are E, tho substituents on the two rings are trans; the stereochemistry of the rings to each other is not known).

Employing; the 10-step method of Example 1, but using 3-oxo-pentanoio acid methyl ester instead of 4- methyl-3-oxo-pentanoic acid methyl ester in step 1, there was obtained the title pyranone product; M.P. 184°–185° C.

NMR (CDCl₃): 6.7–6.9δ(multiplet, 4 protons); 6.17 (doublet, J=16.2 Hz, 2 protons); 5.17 (doublet of doublets, J=16.2 Hz, J=6 Hz, 2 protons); 4.7–4.9 (multiplet, 4 protons); 3.9–4.0 (multiplet, 2 protons); 2.66 (quintet, J=7.5 Hz, 4 protons); 2.39 (doublet, J=4 Hz); 1.2–1.6 (multiplet, 4 protons); 1.08 (triplet, J=7.5 Hz, 6 protons).

Infrared spectrum: Principal absorption at 3400, 1719, 1605, 1511, 1253, and 1041 reciprocal centimeters.

Mass spectrum: M/z (% base peak): 509(3.1), 448(10), 421(33), 406(13), 394(100).

EXAMPLE 3

Preparation of [R*,S*(E)]7,7'-[2,6-diethyl-4-(4-fluorophenyl)-3,5-pyridinediyl]bis[3,5-dihydroxy-6-heptenoic acid, disodium salt]

384 Mg (0.72 m mol) of the title pyranone product of Example 2 was dissolved in 2.5 ml of tetrahydrofuran and 1.43 ml 1N sodium hydroxide solution was added, together with a small amount of ethanol to ensure homogeneity. After stirring for 60 minutes at room temperature, the solvents were removed under vacuum. Twice, methanol was added to the residue and evaporated to dryness to remove the last traces of water to yield the title heptanoic acid sodium salt product.

NMR(D₂O): 7.1–7.2 δ(multiplet, 4 protons); 6.42(doublet, J=16.2 Hz, 2 protons); 5.38 (doublet of doublets, J=16.2 Hz, J=6 Hz, 2 protons); 4.20 (quintet, J=7.2 Hz, 2 protons); 3.5–3.65 (multiplet, 2 protons); 2.84 (quintet, J=7.5 Hz, 4 protons); 2.15–2.3 (multiplet, 4 protons); 1.3–1.65 (multiplet, 4 protons), 1.21 (triplet, J=7.5 Hz, 6 protons).

Infrared spectrum: Principal absorption at 3400, 2936, 1578, 1408, and 1222 reciprocal centimeters.

Mass spectrum: M/z (% base peak): 509 (3.1), 480 (2.3), 448 (10), 421 (33), 406 (13), 394 (100), 376 (32.6).

I claim:

1. A compound of Formula I

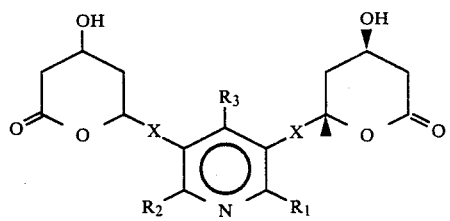

wherein X is —CH₂CH₂— or —CH=CH—;
wherein R₁ R₂ are the same and are selected from
(a) alkyl of from one to six carbons;
(b) trifluoromethyl;
(c) cyclopropyl
(d) cyclohexyl;
(e) cyclohexylmethyl;
(f) NR'R" wherein R' and R" are each independently hydrogen, alkyl of from one to four carbon atoms, or together with the N to which they are attached from

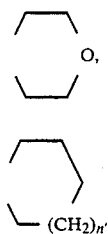

wherein n' is an integer of from 0 to 5,

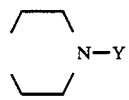

wherein Y is hydrogen or an alkyl of from one to four carbon atoms;
(g) phenyl;
(h) phenyl substituted with
  fluorine,
  chlorine,
  bromine,
  hydroxy,
  trifluoromethyl,
  alkyl of from one to four carbon atoms, or
  alkoxy of from one to four carbon atoms;
(i) phenylmethyl;
(j) phenylmethyl substituted with
  fluorine,
  chlorine,
  bromine,
  hydroxy,
  trifluoromethyl,
  alkyl of from one to four carbon atoms, or
  alkoxy of from one to four carbon atoms;
wherein R₃ is
(a) alkyl of from one to six carbons;
(b) trifluoromethyl;
(c) cyclopropyl;
(d) cyclohexyl
(e) cyclohexylmethyl;
(f) phenyl;
(g) phenyl substituted with
  fluorine;
  chlorine,
  bromine,
  hydroxy,
  trifluoromethyl,
  alkyl of from one to four carbon atoms, or
  alkoxy of from one to four carbon atoms;
(h) phenylmethyl;
(i) phenylmethyl substituted with
  fluorine,
  chlorine,
  bromine,
  hydroxy,
  trifluoromethyl,
  alkyl of from one to four carbon atoms. or
  alkoxy of from one to four carbon atoms;
or the corresponding N-oxide, all of the compounds being in the trans racemate of the tetrahydropyran moiety.

2. A compound as defined by claim 1 wherein X is —CH=CH—.

3. A compound as defined by claim 1 wherein X is —CH$_2$CH$_2$—.

4. A compound as defined by claim 1 having the name 6,6'-[[2,6-bis(1-methylethyl)-4-(4-fluorophenyl)-3,5-pyridinediyl]di-1,2-ethenediyl]bis[4α,6B(E)][tetrahydro-4-hydroxy-2H-pyran-2-one].

5. A compound as defined in claim 1 having the name 6,6'-[2,6-diethyl-4-(4-fluorophenyl)-3,5-pyrdinedyl]bis[-4α,6B(E)][2,1-ethenediyl]bis[tetrahydro-4-hydroxy-2H-pyran-2-one].

6. A pharmaceutical composition for inhibiting cholesterol biosynthesis comprising an effective cholesterol inhibiting amount of a compound as defined by claim 1 in combination with a pharmaceutically acceptable carrier.

7. A method of inhibiting cholesterol biosynthesis in a patient in need of said treatment comprising administering a cholesterol synthesis inhibiting amount of a compound as defined by claim 1 in combination with a pharmaceutically acceptable carrier.

* * * * *